(12) United States Patent
Lin et al.

(10) Patent No.: US 11,564,633 B2
(45) Date of Patent: Jan. 31, 2023

(54) STATE ASSESSMENT SYSTEM, DIAGNOSIS AND TREATMENT SYSTEM, AND METHOD FOR OPERATING THE DIAGNOSIS AND TREATMENT SYSTEM

(71) Applicant: INDUSTRIAL TECHNOLOGY RESEARCH INSTITUTE, Hsinchu (TW)

(72) Inventors: Chii-Wann Lin, Hsinchu (TW); Kuo-Chun Lee, Hsinchu (TW); Jung-Chuan Pan, Hsinchu (TW); Heng-Jie Wang, Hsinchu (TW); Wei-Zheng Lu, Hsinchu (TW); Po-An Hsu, Hsinchu (TW); Kun-Ta Wu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 529 days.

(21) Appl. No.: 16/720,249

(22) Filed: Dec. 19, 2019

(65) Prior Publication Data
US 2020/0214642 A1 Jul. 9, 2020

Related U.S. Application Data

(60) Provisional application No. 62/783,300, filed on Dec. 21, 2018.

(30) Foreign Application Priority Data

Dec. 18, 2019 (TW) ................................. 108146476

(51) Int. Cl.
*A61B 5/00* (2006.01)
*G16H 50/50* (2018.01)
(Continued)

(52) U.S. Cl.
CPC .............. *A61B 5/7264* (2013.01); *A61B 1/24* (2013.01); *A61B 5/0205* (2013.01); *A61B 5/486* (2013.01);
(Continued)

(58) Field of Classification Search
CPC ....... A61B 5/7264; A61B 1/24; A61B 5/0205; A61B 5/4836; A61B 5/4854; A61B 5/486;
(Continued)

(56) References Cited

U.S. PATENT DOCUMENTS 7,337,000 B2 * 2/2008 Meyer ................. A61B 5/7264
600/510
8,457,706 B2 * 6/2013 Baker, Jr. ............... G16H 50/20
600/323
(Continued)

FOREIGN PATENT DOCUMENTS

| CN | 2796742 | 7/2006 |
|---|---|---|
| CN | 100398083 | 7/2008 |

(Continued)

OTHER PUBLICATIONS

Qu, et al. "Automatic Tongue Image Segmentation for Traditional Chinese MedicineUsing Deep Neural Network", Intelligent Computing Theories and Application, ICIC 2017; 2017; 247-259.
(Continued)

*Primary Examiner* — Jerome Grant, II
(74) *Attorney, Agent, or Firm* — Amin, Turocy & Watson, LLP (57) ABSTRACT

A state assessment system, a diagnosis and treatment system and a method for operating the diagnosis and treatment system are disclosed. An oscillator model converts a physiological signal of a subject into a defined feature image. A classification model analyzes state information of the subject
(Continued)

based on the feature image. An analysis model outputs a treatment suggestion for the subject based on the state information of the subject. An AR projection device projects acupoint positions of a human body onto the subject, for the subject to be treated based on the treatment suggestion.

21 Claims, 7 Drawing Sheets (51) Int. Cl.
*G16H 50/30* (2018.01)
*G16H 30/40* (2018.01)
*G16H 50/20* (2018.01)
*A61B 5/0205* (2006.01)
*G16H 20/30* (2018.01)
*A61B 1/24* (2006.01)
*A61N 1/365* (2006.01)
*A61B 5/024* (2006.01)
*A61B 5/08* (2006.01)
*A61B 90/00* (2016.01)

(52) U.S. Cl.
CPC .......... *A61B 5/4836* (2013.01); *A61B 5/4854* (2013.01); *A61B 5/7267* (2013.01); *A61B 5/7425* (2013.01); *G16H 20/30* (2018.01); *G16H 30/40* (2018.01); *G16H 50/20* (2018.01); *G16H 50/30* (2018.01); *G16H 50/50* (2018.01); *A61B 5/0077* (2013.01); *A61B 5/0088* (2013.01); *A61B 5/024* (2013.01); *A61B 5/08* (2013.01); *A61B 2090/365* (2016.02); *A61N 1/36585* (2013.01)

(58) Field of Classification Search
CPC ... A61B 5/7267; A61B 5/7425; A61B 5/0077; A61B 5/0088; A61B 5/024; A61B 5/08; A61B 2090/365; A61B 5/0245; A61B 5/14542; A61B 5/316; A61B 5/489; A61B 5/6803; A61B 5/681; A61B 5/6824; A61B 2562/0233; A61B 5/004; A61B 5/02007; A61B 5/02405; A61B 5/0816; A61B 5/7257; A61B 90/36; A61B 2017/00699; A61B 2017/00703; A61B 2090/366; A61B 2090/372; A61B 2090/502; G16H 20/30; G16H 30/40; G16H 50/20; G16H 50/30; G16H 50/50; G16H 30/20; A61N 1/36585; A61N 1/36014; A61H 2201/1207; A61H 1/00; A61H 39/02; G06T 7/0012; G06F 3/011; G06K 9/6267; G06V 2201/03
USPC .......................................................... 706/924
See application file for complete search history.

(56) References Cited

U.S. PATENT DOCUMENTS

| 9,390,630 | B2 | | 7/2016 | Daniels | |
|---|---|---|---|---|---|
| 9,655,593 | B2 | * | 5/2017 | Kawashima | .......... A61B 8/5223 |
| 11,004,461 | B2 | * | 5/2021 | Howard | .................. G10L 25/63 |
| 11,324,444 | B2 | * | 5/2022 | Jensen | .................. A61B 5/291 |
| 2016/0148052 | A1 | | 5/2016 | Tsuda et al. | |
| 2016/0324488 | A1 | | 11/2016 | Olsen | |
| 2018/0300919 | A1 | | 10/2018 | Muhsin et al. | |
| 2019/0050985 | A1 | * | 2/2019 | Den Brinker | ........ A61B 5/0295 |

FOREIGN PATENT DOCUMENTS

| CN | 100488448 | | 5/2009 | |
|---|---|---|---|---|
| CN | 102813555 | | 12/2012 | |
| CN | 105614831 | | 6/2016 | |
| CN | 105825064 | | 8/2016 | |
| CN | 106251381 | | 12/2016 | |
| CN | 106327983 | | 1/2017 | |
| CN | 106859767 | | 6/2017 | |
| CN | 106859797 | | 6/2017 | |
| CN | 107102728 A | * | 8/2017 | ............. G06F 3/011 |
| CN | 107221000 | | 9/2017 | |
| CN | 107242857 | | 10/2017 | |
| CN | 108379064 | | 8/2018 | |
| CN | 109948396 | * | 6/2019 | ............. G06K 9/00 |
| EP | 3207862 | * | 8/2017 | ............. A61B 5/103 |
| JP | 2015202208 | * | 11/2015 | ............. A61B 5/00 |
| KR | 10-1853190 | | 4/2018 | |
| TW | 581671 | | 4/2004 | |
| TW | I276426 | | 3/2007 | |
| TW | I500411 | | 9/2015 | |
| TW | I501111 | | 9/2015 | |
| TW | 201742597 | | 12/2017 | |
| WO | WO2016096518 | * | 6/2016 | ............. A61M 21/00 |

OTHER PUBLICATIONS

Taiwanese Office Action for Taiwanese Patent Application No. 108146476 dated Nov. 24, 2020.

* cited by examiner

STATE ASSESSMENT SYSTEM, DIAGNOSIS AND TREATMENT SYSTEM, AND METHOD FOR OPERATING THE DIAGNOSIS AND TREATMENT SYSTEM

CROSS-REFERENCE TO RELATED APPLICATIONS

This application claims priority to Taiwanese Application Serial No. 108146476, filed on Dec. 18, 2019 and U.S. Provisional Application Ser. No. 62/783,300, FILED ON Dec. 21, 2019. The entirety of the above-mentioned applications are hereby incorporated by reference herein and made a part of this specification.

BACKGROUND

1. Technical Field

The present disclosure relates to health evaluation techniques, and, more particularly, to a state assessment system, a diagnosis and treatment system and a method for operating the diagnosis and treatment system.

2. Description of Related Art

A sphygmomanometer, a weighing scale and a clinical thermometer are health measurement instruments commonly used at home. These health measurement instruments provide data that they measure. Most people do not have enough medical background to understand their health conditions based on the data. Therefore, they have to go to a clinic or a medical center to seek medical professional's treatment suggestion. However, it takes time to conduct health examination, and people cannot know their health conditions in real time.

Therefore, how to let people know their health conditions in real time and get appropriate treatment is becoming an urgent issue recently.

SUMMARY

The present disclosure provides a state assessment system, comprising: a signal capturing device configured for capturing a physiological signal of a subject; and an evaluation device, comprising: an oscillator model configured for converting the physiological signal into a feature image; and a classification model configured for classifying state information of the subject based on the feature image.

The present disclosure also provides a diagnosis and treatment system, comprising: a signal capturing device configured for capturing a physiological signal of a subject; and an augmented reality apparatus, comprising: an oscillator model configured for converting the physiological signal into a feature image; a classification model configured for classifying state information of the subject based on the feature image; and an analysis model configured for outputting a treatment suggestion for the subject based on the state information of the subject.

The present disclosure further provides a method for operating a diagnosis and treatment system, comprising: using a signal capturing device to capture a physiological signal of a subject; using an oscillator model to convert the physiological signal into a feature image; using a classification model to classify state information of the subject based on the feature image; and using an analysis model to output a treatment suggestion for the subject based on the state information of the subject.

According to the present disclosure, the oscillator model converts the physiological signal of the subject into the feature image, the classification model analyzes the state information of the subject based on the feature image, the analysis model generates a treatment suggestion for the subject based on the state information, the AR projection device projects the acupoint positions of the human body onto the image of the subject displayed on the displaying device of the AR apparatus, and the infrared radiation device projects the infrared radiation to allow the blood vessels of the subject to be shown on the body surface. Therefore, the blood vessels can be evaded, and the subject can be treated according to the treatment suggestion.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
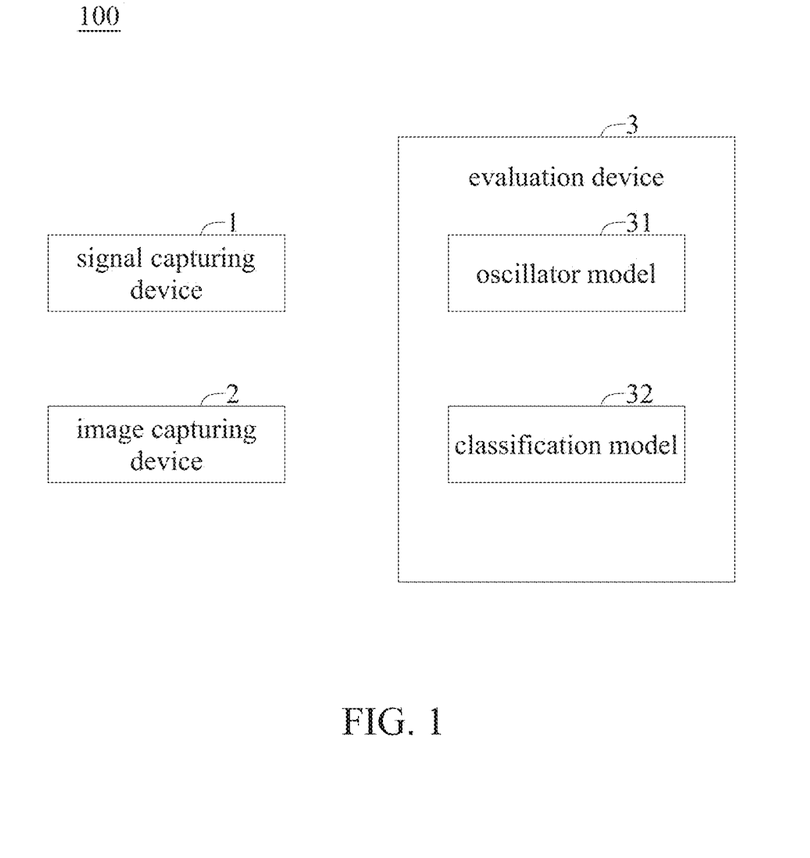
FIG. 1 is functional block diagram of a state assessment system according to the present disclosure.

FIG. 1 is a functional block diagram of a state assessment system 100 according to the present disclosure. As shown in FIG. 1, the state assessment system 100 comprises a signal capturing device 1, an image capturing device 2 and an evaluation device 3, which are connected together in a wired or wireless manner and transmit data. Please also refer to FIG. 2.

The signal capturing device 1 measures a subject and captures a physiological signal of the subject. In an embodiment, the physiological signal includes a heartbeat signal, a respiratory signal and an oximetry ($S_pO_2$), the heartbeat signal is an electrocardiography (ECG), as denoted by a block 21 shown in FIG. 2, and the respiratory signal is a respiratory frequency graph, as denoted by a block 20 shown in FIG. 2.

The image capturing device 2 captures and converts a facial image and a tongue image of the subject into a facial feature image and a tongue feature image, respectively. In an embodiment, the facial feature image includes pixel information of every position of the face, and the tongue feature image includes pixel information of every position of the tongue.

In an embodiment, the physiological signal changes with time. For example, the wavelength of the respiratory frequency graph in block 20 is 10 seconds (capturing the respiratory frequency of the subject), and the wavelength of the electrocardiography in block 21 is 1 second (capturing the heartbeat of the subject, QRS wave group representing the heartbeat information; or capturing the arterial pulse signal of the subject). The so-called feature image does not change with time, and can be a one-dimensional (1D) image, a two-dimensional (2D) image or a three-dimensional (3D) image. In an embodiment, the feature image is a 3D image, as shown in FIGS. 3A to 3D. The feature image is coupled by the heartbeat signal and the respiratory signal to become a feature image with heartbeat and respiratory coupled.

Figure 2:
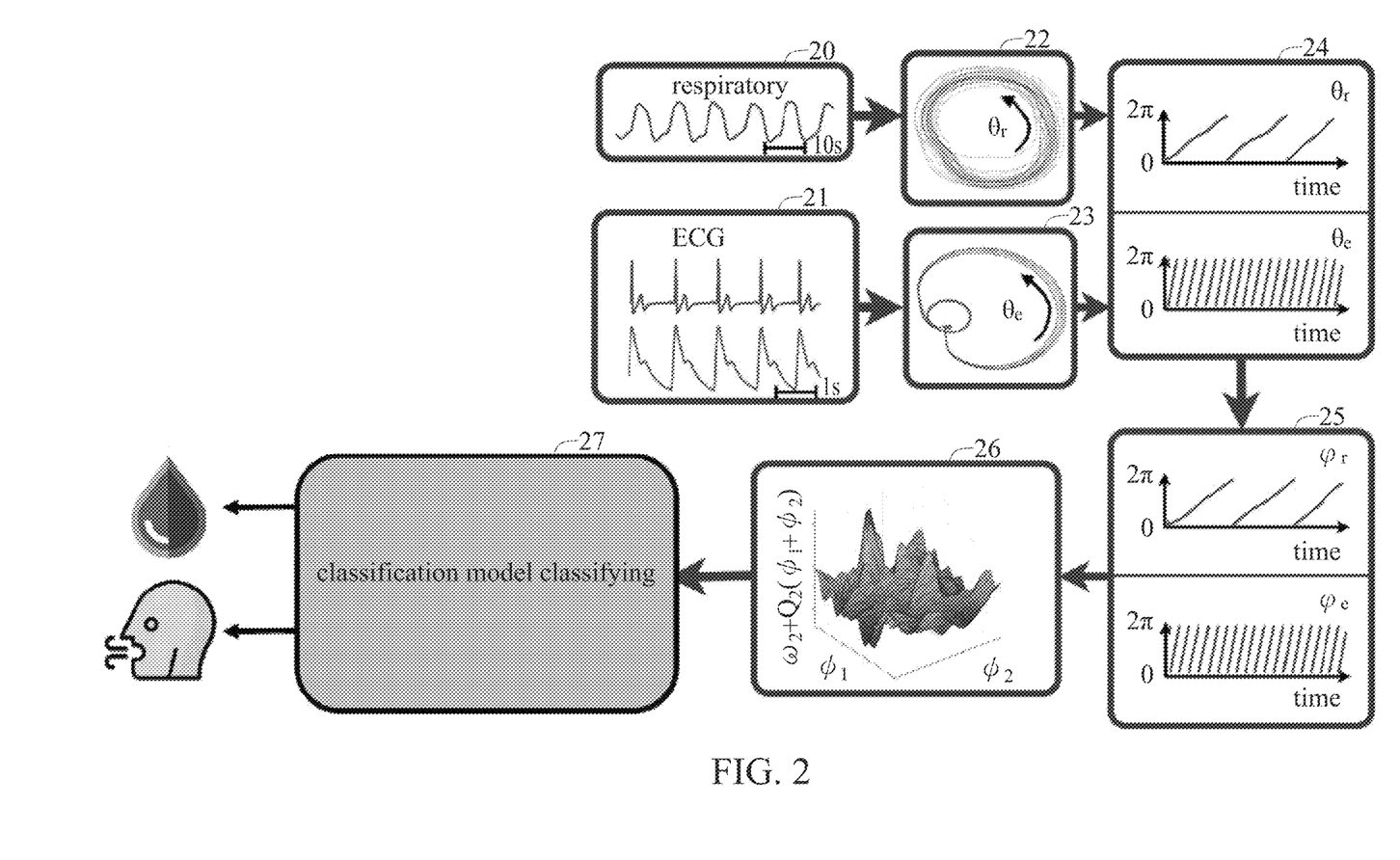
FIG. 2 is a flow chart illustrating generating a feature image in a state assessment system according to the present disclosure.

The evaluation device 3 comprises an oscillator model 31 and a classification model 32. The oscillator model 31 converts the physiological signal into a feature image. The classification model 32 classifies state information of the subject based on at least one feature image. FIG. 2 illustrates the oscillator model 31 converting the physiological signal into the feature image.

The oscillator model 31 includes blocks 20 to 26. Since the heartbeat signal (block 21) and the respiratory signal (block 20) of the subject change with time, the protophase of the respiratory signal (block 20) is a respiratory protophase $\theta_r$, which oscillates cyclically with time. The protophase of the heartbeat signal (block 21) is a heartbeat protophase $\theta_e$, which oscillates cyclically with time. The respiratory protophase $\theta_r$, and the heartbeat protophase $\theta_e$ (frequency space) are converted and depicted with time (time space), with a maximum amplitude of $2\pi$ (a complete period, for example, between two R waves of the heartbeat signal). The upper diagram in the block 24 is that the respiratory protophase $\theta_r$ is depicted with amplitude vs time. The respiratory protophase $\theta_r$ and the heartbeat protophase $\theta_e$ are converted into the phase $\varphi_r$ of a respiratory signal and the phase $\varphi_e$ of a heartbeat signal, respectively. Block 25 represents depicting a graph changing with time, with an amplitude of $2\pi$. The upper diagram in the block 25 is the phase $\varphi_r$ of a respiratory signal, and the lower diagram in the block 25 is the phase $\varphi_e$ of a heartbeat signal. Two oscillation systems are coupled or interacted according to equations (1) and (2), to form a feature image of block 26, where X axis and Y axis represent the phase $\varphi_r$ of the respiratory signal and the phase $\varphi_e$ of the heartbeat signal, respectively, and Z axis is the measurement value after the two oscillation systems are coupled according to equation (2). The oscillator model 31 converts the heartbeat signal (block 21) and the respiratory signal (block 20) of the subject into the heartbeat protophase (block 23) and the respiratory protophase (block 22), respectively. And then the oscillator model 31 couples two independent oscillation systems to become a 3D feature image with the respiratory and heartbeat coupled and interacted (e.g., block 26). The classification model 32 (block 27) analyzes the state information of the subject based on the feature image of the subject with the heartbeat and respiratory coupled. The classification model 32 (block 27) also analyzes at least one of the facial feature image and the tongue feature image of the subject received from the image capturing device 2. In an embodiment, the classification model 32 is a convolutional neural network (CNN) or a support vector machine (SVM). The classification model 32 is trained based on the coupled 3D feature image (block 26), the facial feature image and the tongue feature image. As such, the symptom of the subject corresponds to the feature image. The classification model 32 determines the state information of the subject based on the feature image. In an embodiment, the state information of the subject includes qi deficiency, qi sufficiency, qi normal, blood deficiency, blood sufficiency and blood normal, which are defined by Chinese medication. The classification model 32 takes collected clinical data (converted by the oscillator model 31 into a 3D feature image) as training data and establishes an affection/disease classification model. The affection/disease classification model classifies the affection/disease type or status of the subject by inputting the heartbeat, respiratory, facial image or tongue feature image of the subject into, for example, qi deficiency, qi sufficiency, qi normal, blood deficiency, blood sufficiency, blood normal etc., to evaluate the health condition.

The oscillator model 31 takes the heart and lungs data as two independent oscillators of the subject as an analysis basis, which can be derived according to equations (1) and (2), where $\varphi_1$ is the phase of a heartbeat signal (equivalent to $\varphi_e$), $\varphi_2$ is the phase of a respiratory signal (equivalent to $\varphi_r$), $q_1$ is a coupling coefficient of the heartbeat signal, $q_2$ is a coupling coefficient of the respiratory signal, $Q_1$ is a coupling function of the heartbeat signal, $Q_2$ is a coupling function of the respiratory signal, $\omega_1$ is a frequency of the heartbeat signal, and $\omega_2$ is a frequency of the respiratory signal. The derivative of the phase $\varphi_1$ of the heartbeat signal is equal to the coupling function $Q_1$ of the heartbeat signal. The derivative of the phase $\varphi_2$ of the respiratory signal is equal to the coupling function $Q_2$ of the respiratory signal. As the two oscillators are extended to more than two oscillators, similar measurement method can also be applied.

$$\dot{\varphi}_1 = Q_1(\varphi_1, \varphi_2) = \omega_1 + q_1(\varphi_1, \varphi_2) \qquad (1), \text{ and}$$

$$\dot{\varphi}_2 = Q_2(\varphi_1, \varphi_2) = \omega_2 + q_2(\varphi_2, \varphi_1) \qquad (2).$$

The oscillator measuring theory employed by the present disclosure is described as follows. Different observing points are measured at different time sequences. The electrocardiography and the pulsebeat of a wrist, or other pulse points are taken to be the observing points. The measured number sequence (e.g., the respiratory frequency of block 20, and the electrocardiography signal of block 21) can be converted by different conversion methods (e.g., Hilbert transform method, Wavelet transform method etc.) into a 2D graph having frequency or phase variation (converted from a time domain to a frequency domain, the respiratory protophase graph shown in block 22, the heartbeat protophase graph shown in block 23, the frequency f and the phase $\varphi$ are interchangeable, e.g., $\omega = 2\pi f$, $\omega$ multiplied by time t is equal to the phase). The 2D graph converted by the time sequence of each observing point represents an image of a limited range. The limited range results from the fact that the oscillation frequency and period of the heart and lungs have basic cadence and regularity. For example, for a physical structure of a human body, the heart has a sinoatrial node (SA Node) as a pacemaker to control the pulse of the heart. The converted and generated 2D graph is a periodical cyclical image of a limited range, such as the 2D graph shown in block 22 of FIG. 2 representing the respiratory, and the 2D graph shown in block 23 representing ECG. The 2D graph is called the protophase ($\theta$). The 2D graphs in blocks 22 and 23 are changed and represented by blocks 24 and 25, respectively, where the oscillation amplitude is $2\pi$ and is drawn as time elapsed.

In an embodiment, the equation of Hilbert transform is converted by the following equations:

$$Z_{ac}(\psi) = \sum_{n=0} Hn e^{i\psi}, \text{ and}$$

-continued $$Hn = \frac{1}{\psi(T)} \int_0^{\psi(T)} z(\psi) e^{-in\psi} d\psi = \frac{1}{T} \int_0^T z(t) e^{-in\psi} \frac{d\psi(r)}{dt} dt.$$

Hn represents the Fourier transformation coefficient of $Z(\psi)$; $Z(t)$ is a signal changing with time, and is herein the respiratory frequency shown in block 20, or the electrocardiography signal shown in block 21; $Z_{ac}(\psi)$ is the converted frequency changing equation; and $\psi(t)$ indicates that the measured argument signal changes with time.

Since different observing points generate different 2D graphs, the protophase can turn to the phase ($\varphi$) of the internal original oscillator via mapping. Equation (3) is used to calculate the internal original oscillator phase ($\varphi$), and the 2D graph shown in block 25 of FIG. 2 is obtained, where Im is an imaginary part, $S_n$ is the Fourier series coefficients $Sn=n^{-1}\Sigma_{j=1}^N e^{-in\theta(t_j)}$, and i is $\sqrt{-1}$. Equation (3) converts the protophase $\theta$ into the internal original oscillator phase $\varphi$. The Equation (3) is used in converting block 24 into block 25, wherein the Equation (3) is used to convert the respiratory protophase $\theta_r$ and the heartbeat protophase $\theta_e$ into the phase $\varphi_r$ of the respiratory signal and the phase $\varphi_e$ of the heartbeat signal, respectively. Different observing points are restored to the internal oscillator phase and correspond to a close value, which is close to the original oscillator phase.

$$\varphi = \theta + 2 \sum_{n=1}^{nF} \text{Im}\left[\frac{S_n}{n}(e^{in\theta} - 1)\right] \quad (3)$$

In the period of the internal original oscillator phase ($\varphi$), the internal original oscillator phase function is converted by the following equation (4) into a 3D image, which is then compared and labelled. By using Equations (1) and (2), two oscillation systems are coupled or interacted with each other. Then, two oscillation systems are managed by equation (4) to become a coupling function. In an embodiment, this 2D image is depicted from the coupling function $Q(\varphi_e, \varphi_r)$ of a heartbeat feature image or a respiratory feature image, where $\varphi_e$ is equivalent to the phase $\varphi_1(\varphi_e=\varphi_1)$ of the heartbeat signal, $\varphi_r$ is equivalent to the phase $\varphi_2(\varphi_r=\varphi_2)$ of the respiratory signa, such as the 3D graph shown in block 26 of FIG. 2, $\varphi_e$ is the original oscillator phase of the heartbeat signal, $\varphi_r$ is the original oscillator phase of the respiratory signal, $t_k$ is a time coefficient, K is a signal coefficient, $$K(x, y) = \exp\left[\frac{n}{2\pi}(\cos x + \cos y)\right],$$

$\Phi_e$ is a time sequence of the phased heartbeat signal, and $\Phi_r$ is a time sequence of the phased respiratory signal.

$$Q(\varphi_e, \varphi_r) = \frac{\sum_{k=1}^N \Phi_e K(\varphi_e - \Phi_e(t_k), \varphi_r - \Phi_r(t_k))}{\sum_{k=1}^N K(\varphi_e - \Phi_e(t_k), \varphi_r - \Phi_r(t_k))} \quad (4)$$

Figure 3A:
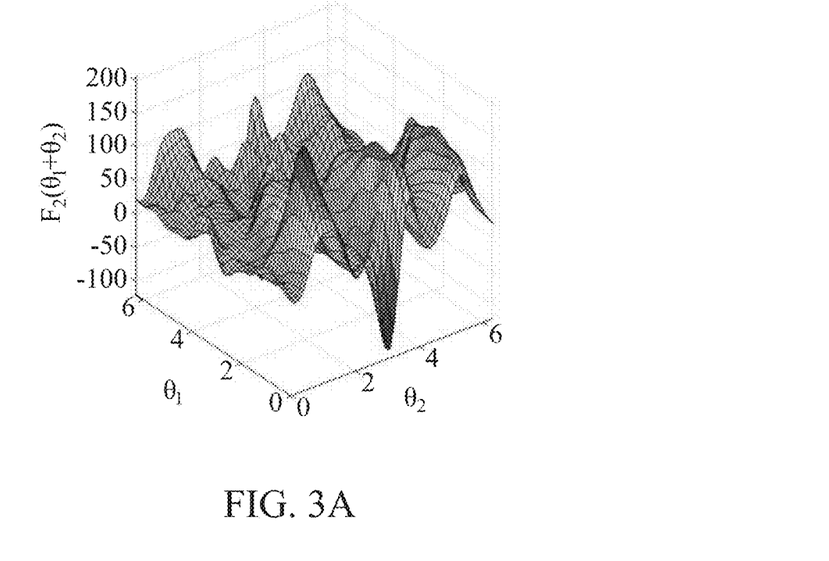
FIGS. 3A to 3D are schematic diagrams of a feature image according to the present disclosure.
Figure 3B:
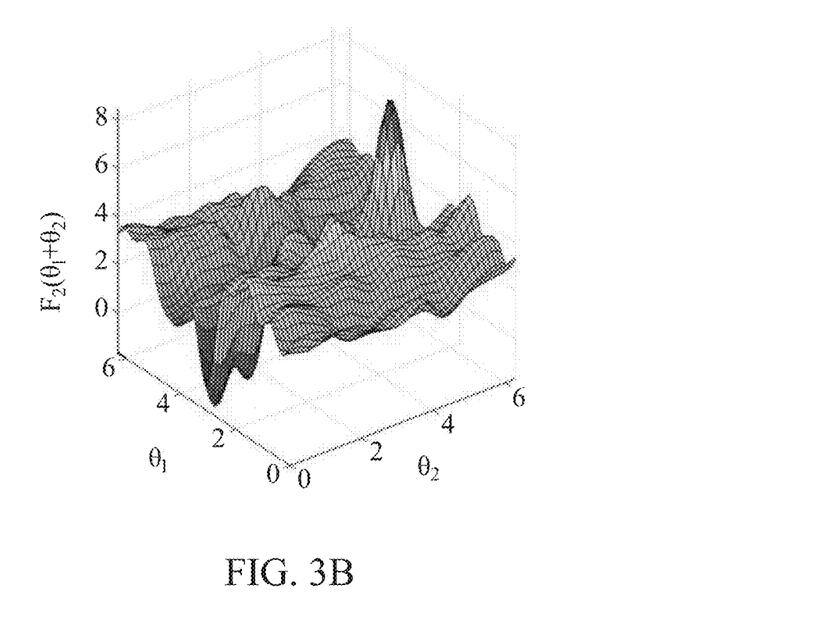
Figure 3C:
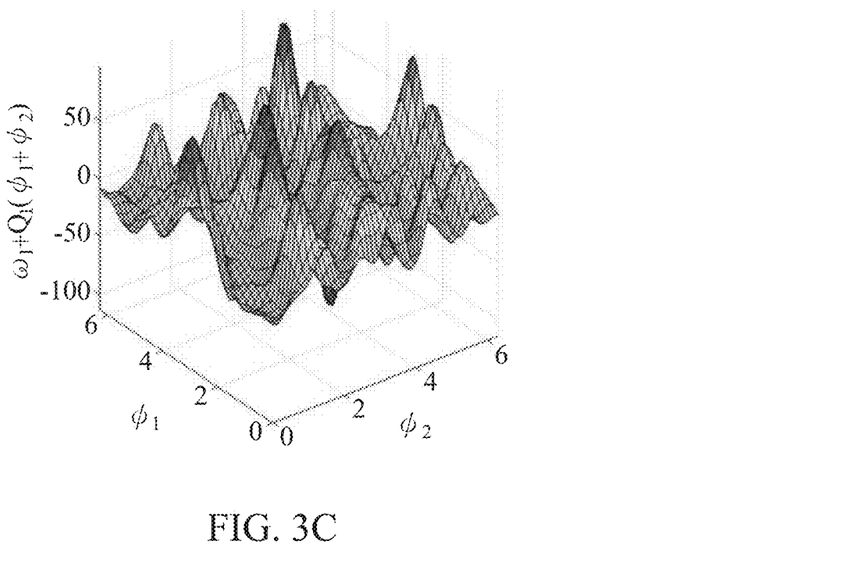
Figure 3D:
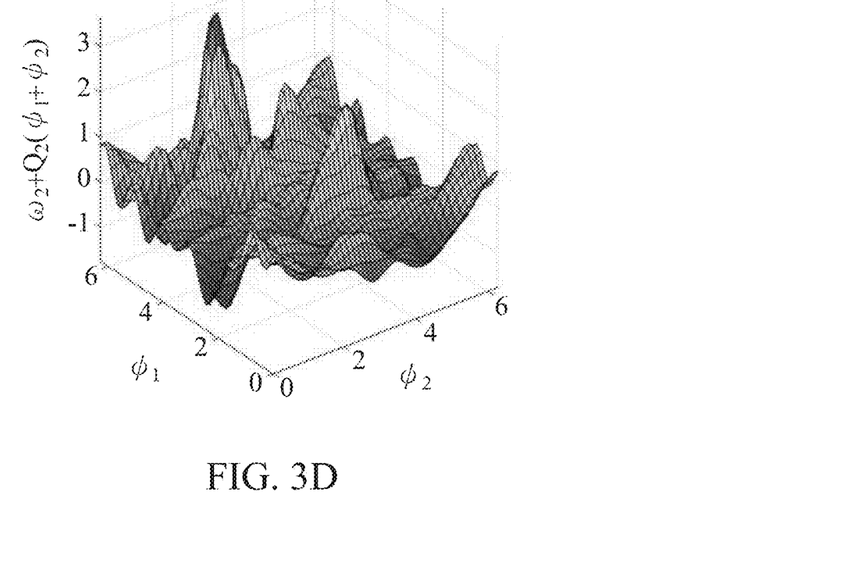

The oscillator model 31 performs the above-described oscillator measuring theory to convert the heartbeat signal and the respiratory signal of the subject into the feature image shown in block 26 of FIG. 2 and the feature image (the heartbeat signal and the respiratory signal are coupled to become a coupling function of the heartbeat and the respiratory, and the coupling function is drawn to become a feature image, and, as such, the feature image is an image with the heartbeat and the respiratory coupled and interacted) shown in FIGS. 3A to 3D, respectively. FIGS. 3A and 3B are the coupling function obtained from the protophase (which is not converted by equation (3), where xy-axis is respiratory and heartbeat protophase $\theta_1$, $\theta_2$, and z-axis is the protophase coupling function $F(\theta_1+\theta_2)$). FIGS. 3C and 3D are the coupling function obtained after being mapped into the phase (converted by equations (1), (2) and (3), where xy-axis is the phase $\varphi_1$ of the respiratory and the phase $\varphi_2$ of the heartbeat, and z-axis is the coupling function). The feature image can describe the space distribution of the so-called "syndrome" in Chinese medication, which is different from the western medication, which measures and obtains an average value. Through this feature image, the present disclosure conducts different clustering or labeling, so as to achieve the showing of the "syndrome" space distribution. For example, block 27 shown in FIG. 2 is entered, and the classification model is used to cluster or label the feature image to be weak, light, mild, medium, average, strong, over etc., which are classified into three states, including deficiency, normal and sufficiency.

In Chinese medication, the measurements at left half of the body and right half of the body or different points represent the relation of different organs, and the variation difference between different measurement points corresponds to different pathology mechanisms. For example, a heartbeat signal corresponds to "blood" in Chinese medication, and a respiratory signal corresponds to "qi." The difference measured at different observing points can be used to show the distribution of the different points in different oscillator phase spaces, and the observed coupling function is able to quantify the space difference between qi and blood. Qi and blood in the phase can be considered as the spaces of phase functions of different oscillators. In other word, this feature image determines three states, i.e., deficiency, normal and sufficiency with regard to two indications, i.e., "qi" and "blood," to further evaluate the "syndrome" contained in the body. In an embodiment, the classification model in block 27 can classify the feature image into qi deficiency, qi sufficiency, qi normal, blood deficiency, blood sufficiency and blood normal.

FIGS. 3A to 3D are feature images calculated according to the above-described process, and the feature images are used as the clustering and classification effects by the subsequent affection/disease classification model (convolutional neural network [CNN], support vector machine [SVM]). The clustering and classification results can be determined based on the similarity measurement done by the vectors calculated by the classification model. In a basic method, a Euclidean distance among vectors is calculated, and outputs of small distances are classified into the same class/group. A clustering algorithm, such as K-means clustering algorithm, can be used to cluster the vectors output by the model. The labeling portion is the clinical data collected in the data collection stage by the medical centers/doctors. A flow chart is established based on a machine learning model, with the clinical data being the training data, which is used for establishing the affection/disease classification model.

Figure 4:
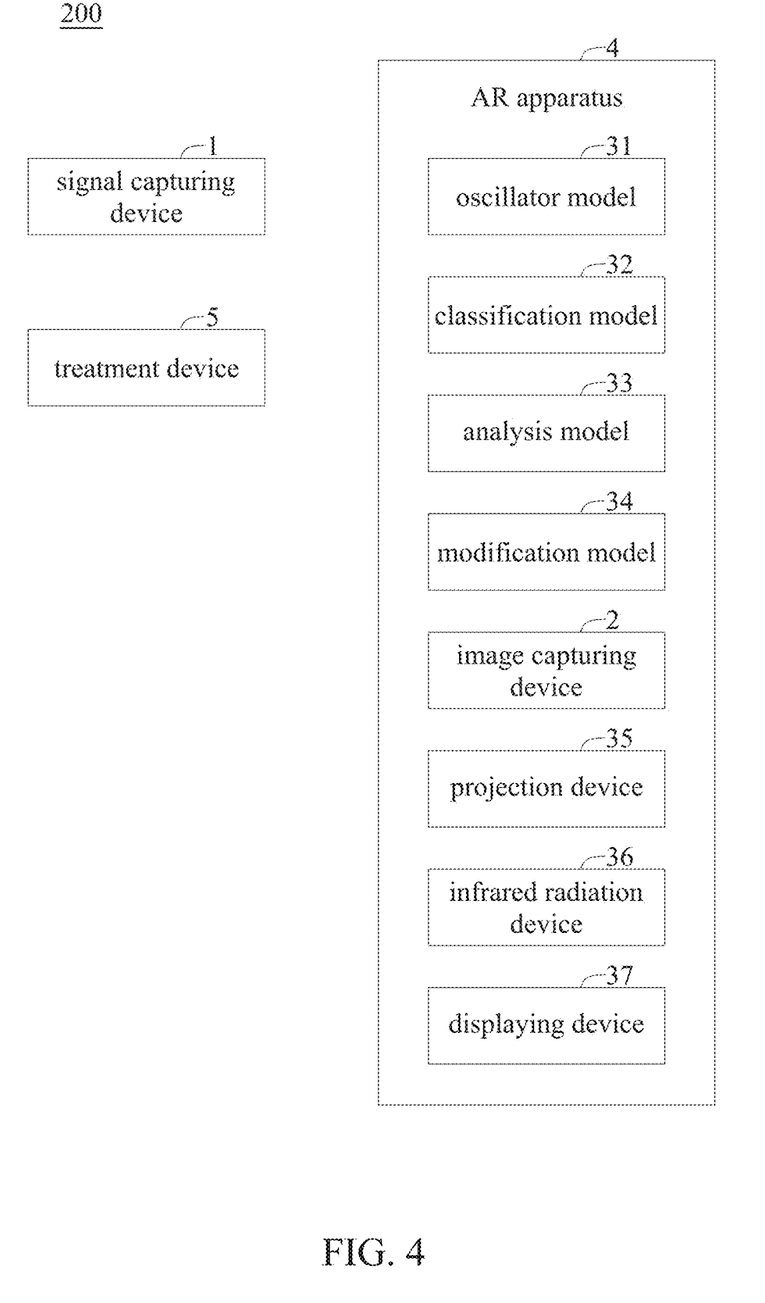
FIG. 4 is a functional block diagram of a diagnosis and treatment system according to the present disclosure.

FIG. 4 is a schematic diagram of a diagnosis and treatment system 200 according to the present disclosure. As shown in FIG. 4, the diagnosis and treatment system 200 includes a signal capturing device 1, an augmented reality (AR) apparatus 4 and a treatment device 5. The signal capturing device 1, the AR apparatus 4 and the treatment device 5 are connected together and transmit data in a wired or wireless manner. The signal capturing device 1 in the diagnosis and treatment system 200 is identical to the signal capturing device 1 in the state assessment system 100, further description thereof hereby omitted.

The AR apparatus 4 comprises an oscillator model 31, a classification model 32, an analysis model 33, a modification model 34, an image capturing device 2, a projection device 35, an infrared radiation device 36 and a displaying device 37, which are connected and transmit data in a wired or wireless manner. The oscillator model 31, the classification model 32 and the image capturing device 2 in the diagnosis and treatment system 200 are identical to the oscillator model 31, the classification model 32 and the image capturing device 2 in the state assessment system 100, further description thereof hereby omitted.

The analysis model 33 obtains the state information of the subject from the classification model 32, and outputs a treatment suggestion and an evaluation treatment result of the subject. In an embodiment, the treatment suggestion of the subject output by the analysis model 33 is acupoints that need to be treated. For example, when qi deficiency is found, the acupoints ST-36, CV-6 and CV-4 are to be treated; when blood deficiency is found, the acupoints SP-6 and K-13 are to be treated; when qi sufficiency is found, the acupoints LR-3 and LR-2 are to be treated; and when blood sufficiency is found, the acupoints SP-10 and LR-8 are to be treated.

The projection device 35 projects the acupoint positions of a human body onto an image of the subject displayed by the displaying device 37 of the AR apparatus 4, allowing a user, when wearing the AR apparatus 4, to see an image with the subject and the acupoint positions of the human body overlapped, and treat the subject based on the acupoint positions.

The infrared radiation device 36 projects infrared radiation to the body of the subject. By using difference of absorption wavelength of infrared light on red blood cells, the infrared radiation can show the positions of the blood vessels of the subject. Therefore, the blood vessels can be evaded when the acupoints of the subject are treated.

The treatment device 5 treats the subject according to the treatment suggestion. In an embodiment, the treatment device 5 is an electric stimulus device, and provides electric stimulus to the acupoints that are required to be treated based on the treatment suggestion.

When the treatment device 5 treats the subject based on the treatment suggestion, the signal capturing device 1 or the image capturing device 2 continues capturing the heartbeat signal, the respiratory signal, the oximetry, the facial image and the tongue image of the subject, the oscillator model 31 continues converting the heartbeat signal and the respiratory signal into the heartbeat feature image and the respiratory feature image, respectively (e.g., the process shown in FIG. 2), and the classification model 32 continues generating the state information of the subject based on at least one feature image.

The modification model 34 classifies the state information of the subject based on the classification model 32, and determines whether to modify the treatment suggestion of the subject output by the analysis model 33.

In an embodiment, the analysis model 33 generates a treatment suggestion that suggests using the treatment device 5 to apply an electric stimulus of 5 W to an acupoint of the subject, and an evaluation treatment result is that the frequency of respiratory is 14 times per minute. Then the projection device 35 can project the acupoint positions of a human body onto the image of the subject displayed on the displaying device 37 of the AR apparatus 4, and the infrared radiation device 36 displays the blood vessels of the subject onto the body surface, to evade the blood vessels when the subject is treated. In treatment stage for the subject, when the state information of the subject analyzed by the classification model 32 does not exceed 14 time per minute, which is evaluated and analyzed by the analysis model 33 for the frequency of the respiratory, the modification model 34 modifies the original power generated by the analysis model 33 to the power that complies with the evaluation treatment result.

Figure 5:
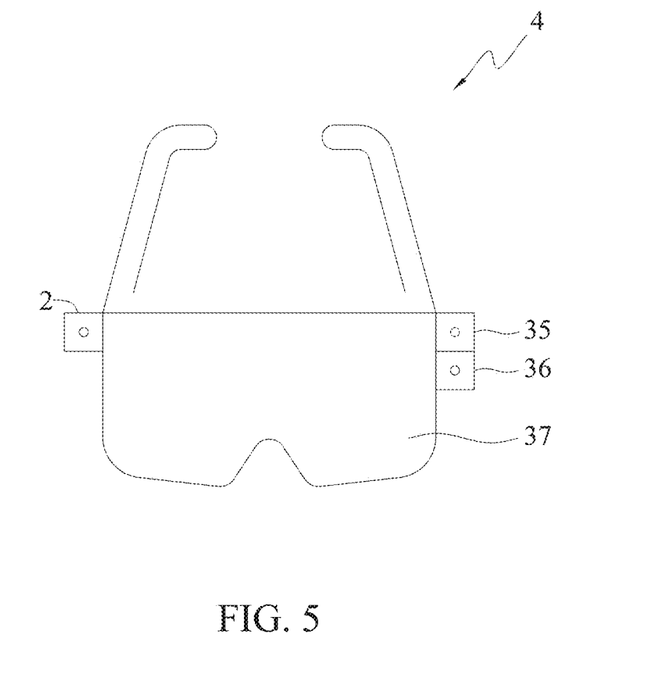
FIG. 5 schematically illustrates an AR apparatus according to the present disclosure.

In an embodiment, the AR apparatus 4 is a head-mounted device, such as the glasses shown in FIG. 5, the projection device 35, the infrared radiation device 36 and the image capturing device 2 are mounted on the glasses, and the displaying device 37 acts as the lenses. The subject or the treater can wear the glasses. When wearing the glasses, the subject (e.g., a patient) can use the treatment device 5, with the help of the functions of the AR apparatus 4, to treat himself. The treater (e.g., a doctor), when wearing the glassed, can use the treatment device 5, with the help of the functions of the AR apparatus 4, to treat the subject.

Figure 6:
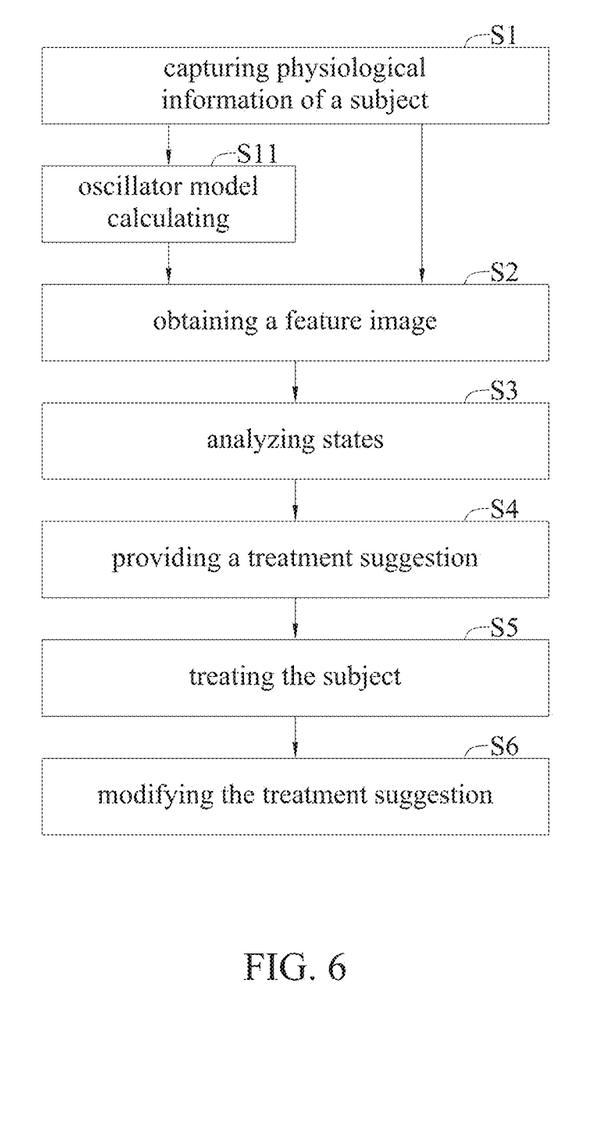
FIG. 6 is a flow chart illustrating a method for operating a diagnosis and treatment system according to the present disclosure.

FIG. 6 is a flow chart of a method of operating a diagnosis and treatment system according to the present disclosure.

In step S1, physiological information of a subject is captured. The physiological information includes a physiological signal (e.g., a heartbeat signal and a respiratory signal), an oximetry, a facial image and a tongue image. The signal capturing device 1 captures the heartbeat signal, the respiratory signal and the oximetry. The image capturing device 2 captures the facial image and the tongue image.

In step S11, the heartbeat signal, the respiratory signal and the oximetry are converted (i.e., calculated by the oscillator model 31). The oscillator model 31 converts the physiological signal into a feature image. In an embodiment, the heartbeat signal and the respiratory signal are coupled to become a feature image with the heartbeat and respiratory coupled (step S2). The image capturing device 2 converts the facial image and the tongue image into the facial feature image and the tongue feature image, respectively, and step S11 is not executed.

In step S3, the states are analyzed. The classification model 32 analyzes the state information of the subject based on at least one of the feature image. In an embodiment, the classification model 32 is a convolutional neural network or a support vector machine, which clusters or labels the feature image (e.g., deficiency, normal, sufficiency etc. in "syndrome" of the Chinese medication).

In step S4, a treatment suggestion is provided. The analysis model 33 obtains the state information of the subject from the classification model 32, and outputs a treatment suggestion and evaluation treatment result of the subject based on the state information of the subject.

In step S5, the treatment is conducted. The treatment device 5 treats the subject based on the treatment suggestion. In an embodiment, the treatment device 5 is an electric stimulus device.

In an embodiment, in step S5 the projection device 35 projects the acupoint positions of a human body onto an image of the subject displayed on the displaying device 37 of the augmented reality apparatus 4, the infrared radiation device 36 projects infrared radiation onto the body of the subject, to show the positions of the blood vessels on the body surface of the subject, and the treatment device 5 treats the subject based on the treatment suggestion.

In step S6, the treatment suggestion is modified. In the treatment stage, steps S1 to S3 are executed, and the modification model 34 modifies the treatment suggestion of the subject output by the analysis model 33 based on the state information of the subject analyzed in step S3 when the subject is treated based on the treatment suggestion.

It is known from the above that in the present disclosure, the oscillator model converts a physiological signal of a subject into a feature image, the classification model analyzes the state information of the subject based on the feature image, the analysis model generates treatment suggestion corresponding to the state information of the subject, the AR projection device projects acupoint positions of a human body onto an image of the subject displayed on the displaying device of the augmented reality apparatus, and the infrared radiation device projects infrared radiation and shows the blood vessels of the subject onto the body surface, to allow evading the blood vessels and treating the subject based on the treatment suggestion.

It will be apparent to those skilled in the art that various modifications and variations can be made to the disclosed embodiments. It is intended that the specification and examples be considered as exemplary, with a true scope of the present disclosure being indicated by the following claims and their equivalents.

What is claimed is:

1. A state assessment system, comprising:
   a signal capturing device configured for capturing a physiological signal of a subject; and
   an evaluation device, comprising:
      an oscillator model configured for converting the physiological signal into a feature image; and
      a classification model configured for classifying state information of the subject based on the feature image,
      wherein the oscillator model calculates the physiological signal to obtain a protophase, an internal original oscillator phase and a coupling function sequentially, and takes the coupling function to be the feature image.

2. The state assessment system of claim 1, wherein the physiological signal comprises a heartbeat signal or a respiratory signal, and the oscillator model couples the heartbeat signal and the respiratory signal to be a feature image with heartbeat and respiratory coupled.

3. The state assessment system of claim 1, further comprising an image capturing device configured for capturing and converting a facial image and a tongue image of the subject into a facial feature image and a tongue feature image, respectively.

4. The state assessment system of claim 1, wherein the classification model is a convolutional neural network or a support vector machine.

5. A diagnosis and treatment system, comprising:
   a signal capturing device configured for capturing a physiological signal of a subject; and
   an augmented reality apparatus, comprising:
      an oscillator model configured for converting the physiological signal into a feature image;
      a classification model configured for classifying state information of the subject based on the feature image; and
      an analysis model configured for outputting a treatment suggestion for the subject based on the state information of the subject,
      wherein the oscillator model calculates the physiological signal to obtain a protophase, an internal original oscillator phase and a coupling function sequentially, and takes the coupling function to be the feature image.

6. The diagnosis and treatment system of claim 5, wherein the physiological signal comprises a heartbeat signal or a respiratory signal, and the oscillator model couples the heartbeat signal and the respiratory signal to be a feature image with heartbeat and respiratory coupled.

7. The diagnosis and treatment system of claim 5, wherein the augmented reality apparatus further comprises an image capturing device configured for capturing and converting a facial image and a tongue image of the subject into a facial feature image and a tongue feature image, respectively.

8. The diagnosis and treatment system of claim 5, wherein the classification model is a convolutional neural network or a support vector machine.

9. The diagnosis and treatment system of claim 5, wherein the augmented reality apparatus further comprises a projection device configured for projecting acupoint positions of a human body onto an image of the subject displayed on a displaying device of the augmented reality apparatus.

10. The diagnosis and treatment system of claim 5, wherein the augmented reality apparatus further comprises an infrared radiation device configured for projecting infrared radiation onto the subject.

11. The diagnosis and treatment system of claim 5, further comprising a treatment device configured for treating the subject based on the treatment suggestion.

12. The diagnosis and treatment system of claim 11, wherein the treatment device is an electric stimulus device.

13. The diagnosis and treatment system of claim 5, wherein the augmented reality apparatus further comprises a modification model configured for modifying the treatment suggestion for the subject output by the analysis model based on the state information of the subject classified by the classification model when the subject is treated based on the treatment suggestion.

14. A method for operating a diagnosis and treatment system, comprising:
   using a signal capturing device to capture a physiological signal of a subject;
   using an oscillator model to convert the physiological signal into a feature image;
   using a classification model to classify state information of the subject based on the feature image; and
   using an analysis model to output a treatment suggestion for the subject based on the state information of the subject,
   wherein the oscillator model calculates the physiological signal to obtain a protophase, an internal original oscillator phase and a coupling function sequentially, and takes the coupling function to be the feature image.

15. The method of claim 14, wherein the physiological signal comprises a heartbeat signal or a respiratory signal, and the oscillator model couples the heartbeat signal and the respiratory signal to be a feature image with heartbeat and respiratory coupled.

16. The method of claim 14, further comprising using an image capturing device to capture and convert a facial image and a tongue image of the subject into a facial feature image and a tongue feature image, respectively.

17. The method of claim 14, further comprising using a projection device to project acupoint positions of a human body onto an image of the subject displayed on a displaying device of an augmented reality apparatus.

18. The method of claim 17, further comprising using an infrared radiation device to project infrared radiation onto the subject.

19. The method of claim 14, further comprising using a treatment device to treat the subject based on the treatment suggestion.

20. The method of claim 19, wherein the treatment device is an electric stimulus device.

21. The method of claim 14, further comprising using a modification model to modify the treatment suggestion for the subject output by the analysis model based on the state information of the subject classified by the classification model when the subject is treated based on the treatment suggestion.

* * * * *